(12) United States Patent
Haas et al.

(10) Patent No.: US 9,317,969 B2
(45) Date of Patent: Apr. 19, 2016

(54) CONSTRUCTIVE ANATOMIC GEOMETRY

(71) Applicant: Varian Medical Systems, Inc., Palo Alto, CA (US)

(72) Inventors: Benjamin M. Haas, Wabern (CH); Micheal Waschbuesch, Rheinfelden (CH); Thomas Coradi, Lenzburg (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 135 days.

(21) Appl. No.: 14/040,536

(22) Filed: Sep. 27, 2013

(65) Prior Publication Data

US 2014/0270426 A1    Sep. 18, 2014

Related U.S. Application Data (60) Provisional application No. 61/798,327, filed on Mar. 15, 2013.

(51) Int. Cl.
| | |
|---|---|
| *G06K 9/00* | (2006.01) |
| *G06T 17/10* | (2006.01) |
| *G06F 19/00* | (2011.01) |
| *H05G 1/42* | (2006.01) |
| *A61N 5/10* | (2006.01) |

(52) U.S. Cl.
CPC .............. *G06T 17/10* (2013.01); *G06F 19/321* (2013.01); *A61N 5/103* (2013.01); *G06T 2210/41* (2013.01)

(58) Field of Classification Search
USPC ......... 382/100, 103, 106, 128–134, 154–155, 382/168, 173, 181, 199, 224, 232, 254, 274, 382/276, 285–291, 305, 312; 378/4, 21, 96, 378/97; 250/363.04; 348/51
See application file for complete search history.

(56) References Cited

U.S. PATENT DOCUMENTS

| | | | | |
|---|---|---|---|---|
| 7,873,223 | B2 | 1/2011 | Binnig et al. | |
| 2004/0195512 | A1* | 10/2004 | Crosetto | A61B 6/037 250/363.04 |
| 2008/0123813 | A1* | 5/2008 | Maurer | A61N 5/103 378/96 |
| 2011/0044524 | A1* | 2/2011 | Wang | G01R 33/54 382/131 |
| 2011/0169924 | A1* | 7/2011 | Haisty | H04N 9/3147 348/51 |
| 2011/0292056 | A1 | 12/2011 | Haas et al. | |
| 2013/0315440 | A1* | 11/2013 | Frank | G06K 9/3216 382/103 |

OTHER PUBLICATIONS

Aristides G. Requicha, "Representations for Rigid Solids: Theory, Methods, and Systems" Computing. Surveys, vol. 12, No. 4, Dec. 1980, 437-464 (28 pages).

\* cited by examiner

*Primary Examiner* — Seyed Azarian
(74) *Attorney, Agent, or Firm* — Vista IP Law Group, LLP (57) ABSTRACT

A method involving an image of an anatomy, includes: obtaining an image of an anatomy; obtaining a program instruction from a user for creating an object in the image; and executing the program instruction to create the object in the image, wherein the act of executing the program instruction is performed using a processor. A computer product having a non-transitory medium storing a set of instructions, an execution of which causes a method to be performed, the method includes: obtaining an image of an anatomy; obtaining a program instruction from a user for creating an object in the image; and executing the program instruction to create the object in the image.

45 Claims, 9 Drawing Sheets

HULL(UNION(MARGINISO("Prostate", 2), MARGINISO("SeminalVesicles", 5)), 15)

FIG. 5

```
s1 = Margin("Prostate", 2)          602
s2 = Margin("SeminalVesicles", 5)   604
u = Union(s1, s2)                   606
return Hull(u, 15)                  608
```

FIG. 6

| | |
|---|---|
| Margin(object, distance)—702 | Returns a new object by adding a margin around the given object |
| Union(object list)—704 | Returns a new object that is the union of the given list of objects |
| Hull(object, curvature)—706 | Returns a new object by generating a hull with maximum given curvature of the given object |
| Smooth(object, radius)—708 | Returns a new object by smoothing the surface of the given object |
| MarginAnisotropic(object, direction, distance)—710 | Returns a new object by adding a margin, only in the given direction, around the given object |
| Subtract(object1, object2)—712 | Returns a new object having all voxels of object1 that are not part of object2 |
| Intersect(object list)—714 | Returns a new object that is the intersection of all objects in the given list |
| Shift(object, vector)—716 | Returns a new object that corresponds to the given object, shifted by the given vector |
| Rotate(object, alpha, phi, theta)—718 | Returns a new object that corresponds to the given object, rotated by alpha, phi, and theta |
| Scale(object, factor)—720 | Returns a new object that corresponds to the given object scaled by factor |
| Block(pos, size)—722 | Returns a new object that has the shape of a block of given size and at given position |
| Sphere(pos, radius)—724 | Returns a new object that has the shape of a sphere of given radius |
| Cylinder(start, end, radius)—726 | Returns a new object that has the shape of a cylinder defined by axis starting and ending point, and radius |

CONSTRUCTIVE ANATOMIC GEOMETRY

RELATED APPLICATION DATA

This application claims priority to and the benefit of U.S. Provisional Patent Application No. 61/798,327, filed on Mar. 15, 2013, the entire disclosure of which is expressly incorporated by reference herein.

FIELD

An embodiment described herein relates to a method, computer product, and an apparatus for operating on a medical image.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Before treatment radiation is delivered to a patient, a treatment plan is created using a treatment planning software. In the treatment planning procedure, a technician may review a medical image, and may draw contours that delineate target volumes and organs at risk. Where available, automatic segmentation may be used to speed up this task and to make delineations more consistent. However, there may be structures that cannot be segmented automatically, and automatic segmentation of structures always require a subsequent manual correction. Correction of automatically generated structures has two parts: correction of anatomical errors and cleanup. The cleanup part often requires a sequence of operations, such as removal of small, isolated parts, smoothing of surfaces, application of margins, and removal of undesired overlap with other structures. These tasks can be repetitive and labor intensive.

Applicant of the subject application believes that a method and an apparatus for operating on a medical image may be desirable.

SUMMARY

A method involving a medical image, includes: obtaining a medical image; obtaining a program instruction from a user for creating an object in the image; and executing the program instruction to create the object in the image, wherein the act of executing the program instruction is performed using a processor.

Optionally, the program instruction is in a form of a script.

Optionally, the program instruction is in a form of a formula.

Optionally, the program instruction is in a form of graphics.

Optionally, the program instruction comprises one or more operators for processing one or more geometric objects.

Optionally, the program instruction comprises one or more mathematical operators.

Optionally, the program instruction comprises one or more logical operators.

Optionally, the program instruction comprises an instruction for one or more loops.

Optionally, the program instruction comprises a conditional instruction.

Optionally, the program instruction is compatible with different medical software from different manufacturers.

Optionally, the program instruction is created using a language that is less versatile than C++ language.

Optionally, the object comprises an anatomical object, and the program instruction comprises instruction for creating a margin around the anatomical object in the image.

Optionally, the program instruction comprises instruction for combining two objects into a single object in the image.

Optionally, the program instruction comprises instruction for a hull operation.

Optionally, the program instruction comprises one or more of a margin operator, an union operator, a hull operator, a smooth operator, a margin anisotropic operator, a subtract operator, an intersect operator, a shift operator, a rotate operator, a scale operator, a block operator, a sphere operator, and a cylinder operator.

Optionally, the act of executing the program instruction is performed during a cleanup procedure in a treatment planning process.

Optionally, the act of executing the program instruction is performed automatically during an automatic segmentation.

Optionally, the object comprises an outline for one or more tissue structures.

Optionally, the obtained image comprises the object, the object being artificially created.

Optionally, the program instruction is stored as a sequence of characters in a first environment, and the method further comprises loading the program instruction in a second environment for execution.

A computer product having a non-transitory medium storing a set of instructions, an execution of which causes a method to be performed, the method includes: obtaining a medical image; obtaining a program instruction from a user for creating an object in the image; and executing the program instruction to create the object in the image.

Optionally, the program instruction is in a form of a script.

Optionally, the program instruction is in a form of a formula.

Optionally, the program instruction is in a form of graphics.

Optionally, the program instruction comprises one or more operators for processing one or more geometric objects.

Optionally, the program instruction comprises one or more mathematical operators.

Optionally, the program instruction comprises one or more logical operators.

Optionally, the program instruction comprises an instruction for one or more loops.

Optionally, the program instruction comprises a conditional instruction.

Optionally, the program instruction is compatible with different medical software from different manufacturers.

Optionally, the program instruction is created using a language that is less versatile than C++ language.

Optionally, the object comprises an anatomical object, and the program instruction comprises instruction for creating a margin around the anatomical object in the image.

Optionally, the program instruction comprises instruction for combining two objects into a single object in the image.

Optionally, the program instruction comprises instruction for a hull operation.

Optionally, the program instruction comprises one or more of a margin operator, an union operator, a hull operator, a smooth operator, a margin anisotropic operator, a subtract operator, an intersect operator, a shift operator, a rotate operator, a scale operator, a block operator, a sphere operator, and a cylinder operator.

Optionally, the act of executing the program instruction is performed during a cleanup procedure in a treatment planning process.

Optionally, the act of executing the program instruction is performed automatically during an automatic segmentation.

Optionally, the object comprises an outline for one or more tissue structures.

Optionally, the obtained image comprises the object, the object being artificially created.

Optionally, the program instruction is stored as a sequence of characters in a first environment, and the method further comprises loading the program instruction into a second environment for execution.

An apparatus includes: a processor configured for obtaining a medical image, obtaining a program instruction from a user for creating an object in the image, and executing the program instruction to create the object in the image; and a non-transitory medium storing the created or modified object.

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

FIG. 7 illustrates examples of operators that may be used in a program instruction for operating on a medical image.

DETAILED DESCRIPTION

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated.

Figure 1:
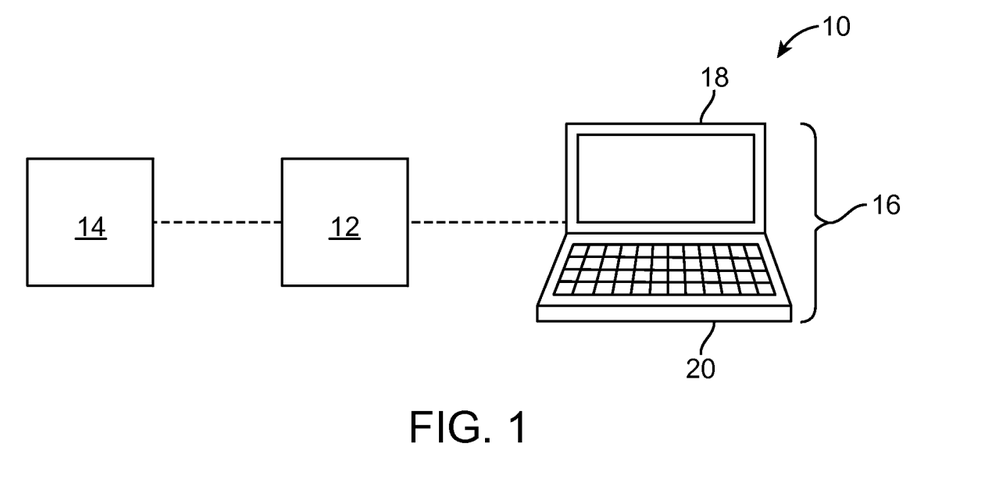
FIG. 1 illustrates an apparatus for performing operations on a medical image.

FIG. 1 illustrates an apparatus 10 for operating on a medical image in accordance with some embodiments. The apparatus 10 includes a processing unit 12, a non-transitory medium for storing data, and a user interface 16 for presenting and receiving information. The processing unit 12 may be implemented using hardware, software, or combination thereof. The non-transitory medium may be a processor readable medium configured to store data associated with an operation of the processing unit 12. The user interface 16 includes a screen 18 for displaying information to a user, and an input device 20 for allowing the user to enter information.

In some embodiments, the apparatus 10 may be a computer (e.g., a desktop, laptop, etc.). In other embodiments, the apparatus 10 may be a mobile device, such as an iPad, a tablet, a smart phone, an iPhone, or any of other handheld devices. In such cases, the screen 18 may be a screen of the mobile device, and the input device 20 may be an input device of the mobile device. In the case of iPad and iPhone, the screen 18 and the input device 20 may be implemented using the touch screen.

Figure 2:
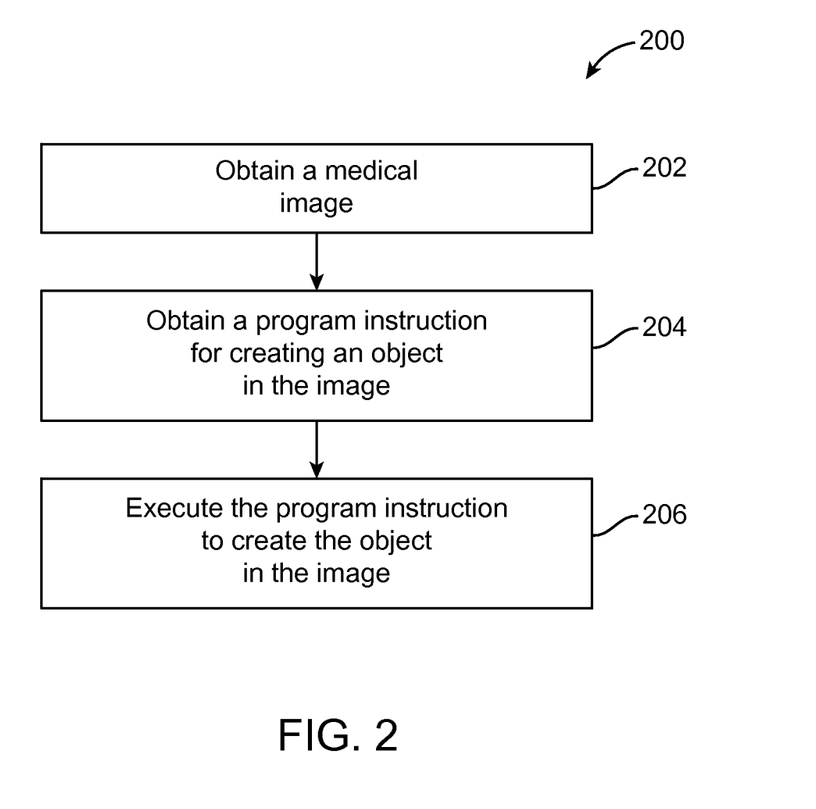
FIG. 2 illustrates a method that involves a medical image.

FIG. 2 illustrates a method 200 for operating on a medical image in accordance with some embodiments. In some embodiments, the method 200 may be performed by the processing unit 12.

First, a medical image is obtained (item 202). By means of non-limiting examples, the medical image may be a x-ray image, a CT image, a PET image, a PET-CT image, a SPECT image, a MRI image, an ultrasound image, or any of other types of images created using different medical imaging techniques. The image may be an image of a human subject. In other embodiments, instead of a human subject, the image may be an image of a non-human subject. Also, in other embodiments, the medical image may be artificially created. For example, in some embodiments, the medical image may include one or more contours (such as a contour drawn around a tissue structure) created by a person.

In some embodiments, the image obtained in item 202 may be created before a treatment session. For example, the image may be created for diagnostic purpose, and/or for treatment planning. In other embodiments, the image may be created during or after a treatment session. For example, the image obtained in item 202 may be created to verify a treatment delivery, and/or to modify a treatment session for future treatment delivery. In some embodiments, the obtaining of the image in item 202 may be performed by the processing unit 12 receiving the image from another device, such as another processing unit, a storage medium (e.g., the medium 14), etc. In other embodiments, the obtaining of the image in item 202 may be performed by a medical imaging device that generates the image.

Figure 3A:
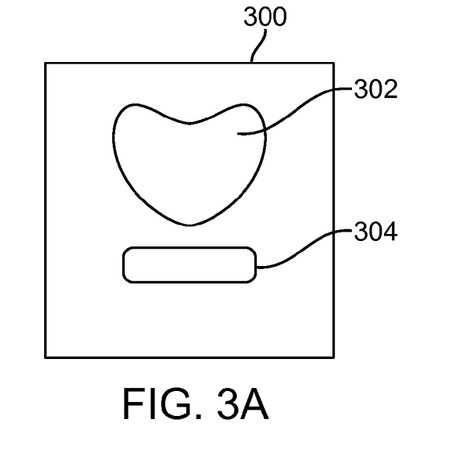
FIGS. 3A-3E illustrate examples of operations being performed on a medical image.

FIG. 3A illustrates an example of a medical image 300 of an anatomy that may be obtained in item 202. The image 300 includes an image of a prostate 302 and an image of seminal vesicles 304. In other examples, the image 300 may include other tissue structure(s).

Returning to FIG. 2, next, a program instruction from a user for creating an object in the image 300 is obtained (item 204). In the illustrated embodiments, the program instruction is created using, or supported by, a unique program language (which may be named "constructive anatomic geometry" or CAG language) that is configured for processing geometric objects. Also, the program instruction for creating the object may be named CAG program instruction. In some embodiments, the CAG program instruction is created by the user, and may be saved as a file for execution by the processing unit 12. For example, a user interface may be presented in the screen 18 of the apparatus 10, which may be a computer (e.g., a desktop, a laptop, etc.), an iPad, a tablet, a smart phone, an iPhone, or any of other handheld devices, for allowing the user to create the program instruction. The program instruction may then be stored in a file. In some embodiments, the file may be transmitted to a processing unit (e.g., the same processing unit that obtains the image in item 202) for execution. The transmission of the file to the processing unit may be performed using an electrical conductor (e.g., which connects the device with the user interface with the processing unit), or wirelessly. In other embodiments, the device 10 for presenting the user interface that allows the user to enter the program instruction may include a processing unit configured to execute the program instruction entered by the user. In such cases, the device 12 that presents the user interface may be the same device that receives the image in item 202.

In some embodiments, the created program instruction may be stored as script text, as a structured file (e.g., in a form of an expression tree), or in any of other formats. In one implementation, the program instruction may be created graphically (e.g., using flow diagrams), and the created program instruction may be converted to a structured file when being saved. Also, in some embodiments, the created program instruction may be shared between different users of medical software, in different versions of a certain medical software, and/or between users of different medical software from different manufacturers (e.g., software providers). For example, in some embodiments, the program instruction may be stored as a sequence of characters in a first environment, and may be loaded into a second environment for execution, wherein the first and second environments may correspond with different software, different users, different work stations, different manufacturers, etc. In further embodiments, different sites (e.g., hospitals, manufacturers, etc.) may use a set of standardized attributes for identifying anatomical structures in images. In such cases, the standardized attributes ensure that an anatomical structure is always identified the same way using CAG language in different program instructions for operating on different medical images.

As shown in FIG. 2, next, the program instruction is executed to create or modify the object in the image (item 206). In some embodiments, the program instruction created using CAG language may be executed by the processing unit 12 (e.g., the same processing unit 12 that obtain the image). Alternatively, the program instruction may be executed by a different processing unit. For example, in other embodiments, the program instruction created using the apparatus 10 may be saved in a file, and the saved program instruction may be transmitted to another processing unit for execution. The transmission of the program instruction may be performed wirelessly (e.g., through a network such as the Internet), or through a wire (e.g., through a cable that connects the apparatus 10 to the other processing unit). In some embodiments, the processing unit that executes the program instruction for operating on the medical image is configured to understand the CAG language (e.g., one or more command, instruction, etc.) of the program instruction.

The CAG program instruction may have different formats in different embodiments. For examples, the program instruction may be in a form of graphics, in a form of a formula, and/or a script.

Figure 3B:
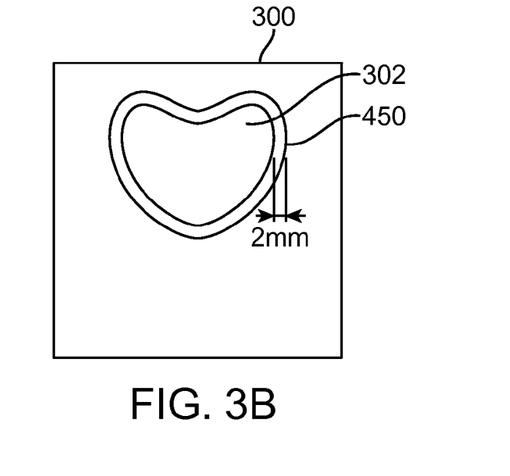
Figure 3C:
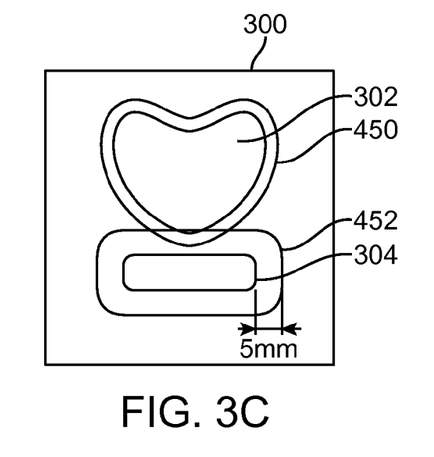
Figure 3D:
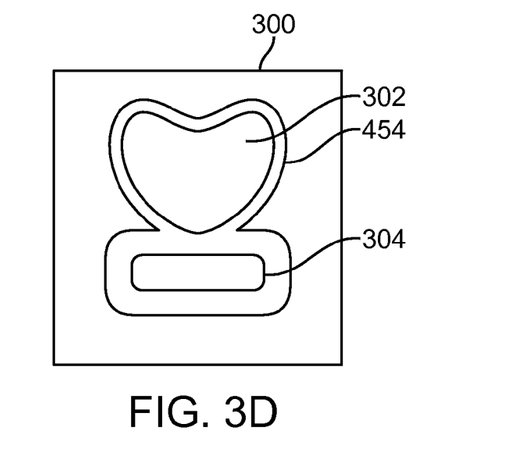
Figure 3E:
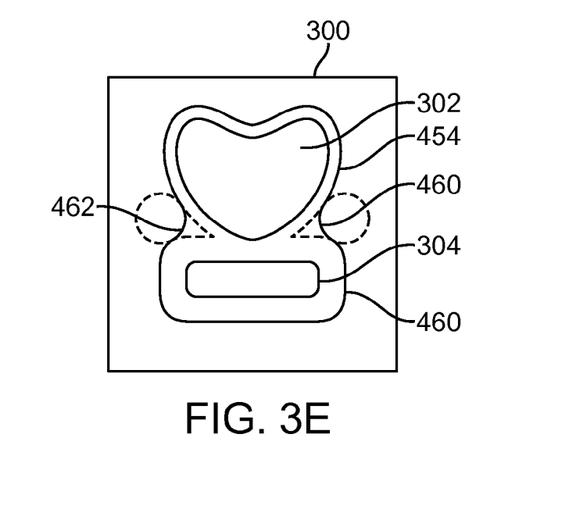
Figure 4:
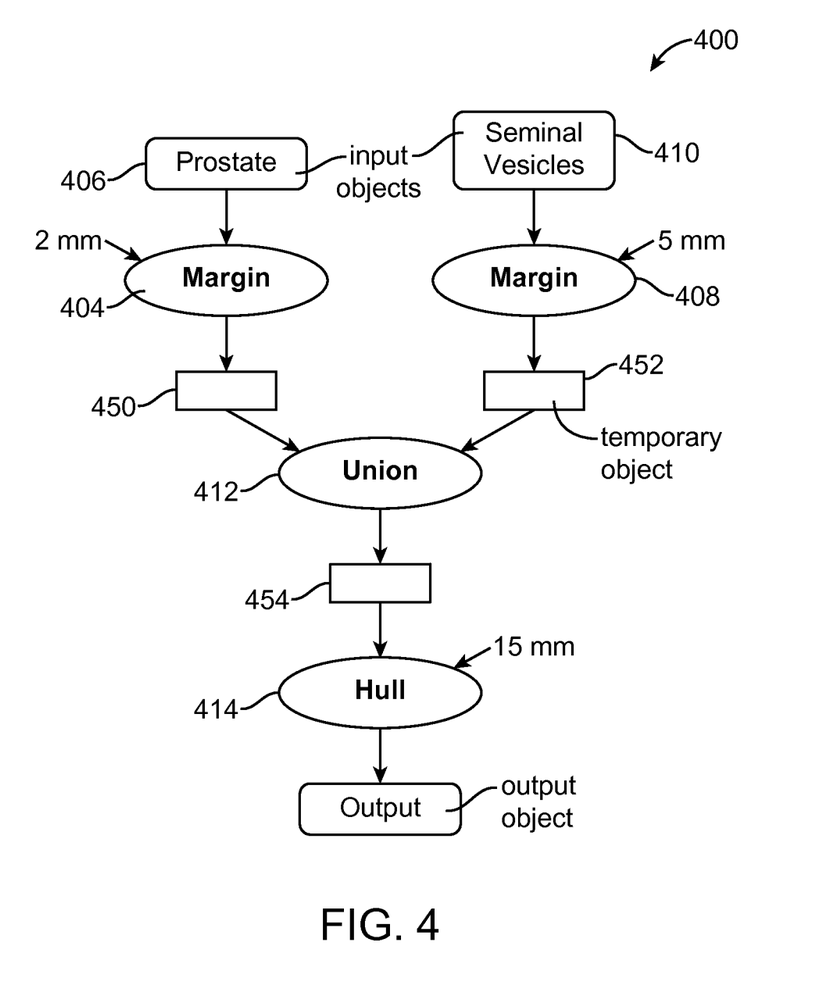
FIG. 4 illustrates an example of a program instruction in graphical form.

FIG. 4 illustrates an example of the CAG program instruction 400 in a graphical form that may be created by the user using the user interface. In the illustrated example, the CAG program instruction 400 includes a margin operator 404 for operating on a prostate image 406, a margin operator 408 for operating on a seminal vesicles image 410, a union operator 412 for combining two images, and a hull operator 414. The CAG program instruction 400 may be saved in a file for execution by the processing unit 12. When the processing unit 12 executes the CAG program instruction 400, the processing unit 12 creates one or more objects based on the command/instruction in the CAG program instruction 400. In the illustrated example, the margin operator 404 prescribes that a 2 mm margin be created around the prostate 302 (or the prostate image 406) in the input image. An example of the created margin 450 around the prostate 302 in the image 300 is illustrated in FIG. 3B. The margin operator 408 prescribes that a 5 mm margin be created around the seminal vesicles 304 (or the seminal vesicles image 410). An example of the created margin 452 around the seminal vesicles 304 in the image 300 is illustrated in FIG. 3C. The union operator 412 prescribes that the output of the margin operator 404 (which is the created margin 450 around the prostate) and the output of the margin operator 408 (which is the created margin 452 around the seminal vesicles) be combined into a single image. FIG. 3D illustrates the object 450 and the object 452 being combined into a single object 454. The object 454 represents a margin around both the prostate 302 and the seminal vesicles 304. The hull operator 414 creates curvilinear segments 460, 462 at corresponding locations in the object 454 where there are sharp corners (FIG. 3E). This results in a new object 460 having a smoother outline.

In some embodiments, a user interface may be provided that allows manual modification of the margins. For example, an initial margin may be conformal to the outline of a structure for which the margin is added. Once the conformal margin is added, the user interface may allow the user to drag various points of the margin outline to increase or decrease distance from the structure.

Also, in some embodiments, after the medical image(s) is processed based on the program instruction (e.g., after margins are added to the medical image set), the treatment plan may be modified according to the modified image(s) because the plan is based on the image(s). Accordingly, the modification of the image(s) may be translated into corresponding changes in the treatment plan.

As shown in the above example, the CAG program instruction in graphical form is advantageous because it is easy to understand, and can be intuitively constructed without substantial difficulties. For example, the flow of the various processing may be achieved simply by connecting various operators and/or input objects using flow arrow(s). In some embodiments, a flow arrow may also be used to create a loop. Thus, a loop processing may be easily prescribed using the graphical form.

Figure 5:
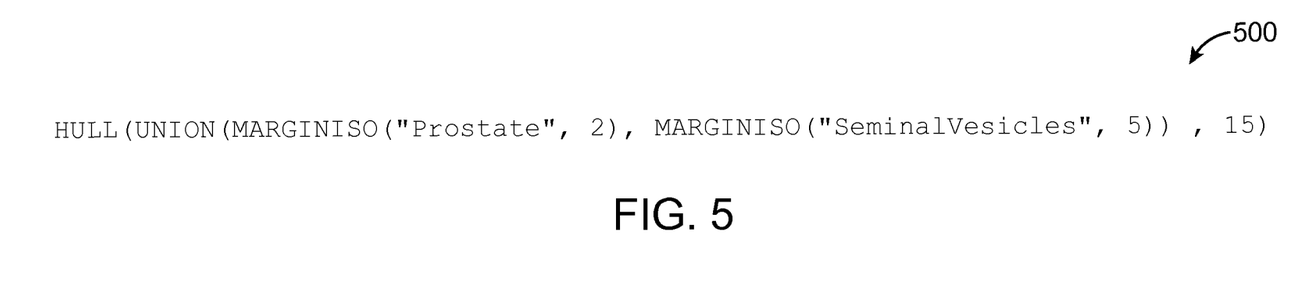
FIG. 5 illustrates an example of a program instruction in formula form.

As discussed, the CAG program instruction may be in a form of a formula in other embodiments. For example, as shown in FIG. 5, the example of the CAG program instruction 400 described in FIG. 4 may be represented as the formula 500: "HULL(UNION(MARGINISO("Prostate", 2), MARGINISO("SeminalVesicles", 5)), 15). The CAG program instruction in the form of the formula 500 of FIG. 5 will create the same output as the program instruction 400 of FIG. 4.

Figure 6:
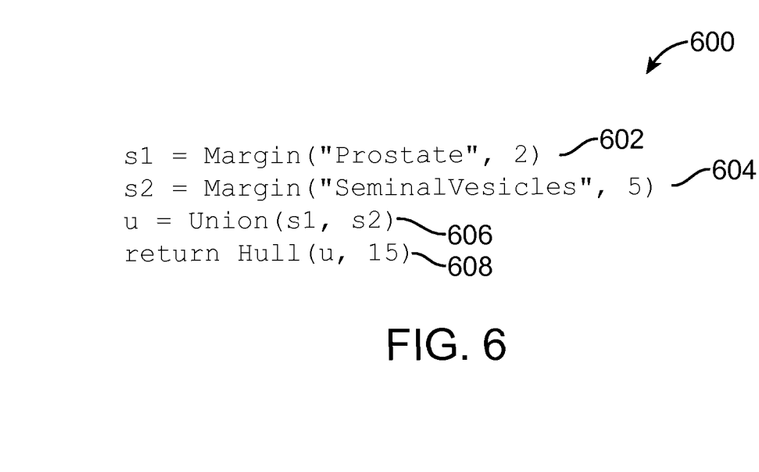
FIG. 6 illustrates an example of a program instruction in a form of a script.

Also, in other embodiments, the example of the CAG program instruction 400 described in FIG. 4 may be in a form of a script 600 like that shown in the example of FIG. 6. The script 600 includes a first script (command line) 602 for creating a margin that is 2 mm away from the prostate, a second script 604 for creating a margin that is 5 mm away from the seminal vesicles, a third script 606 for combining the created margin around the prostate and the created margin around the seminal vesicles to obtain a combined object, and a fourth script 608 for performing a hull operation on the combined object. Thus the CAG program instruction in the form of the script 600 of FIG. 6 will create the same output as the CAG program instruction 400 of FIG. 4.

In some embodiments, it may be beneficial to restrict the complexity of the CAG program instruction. For example, in some embodiments, the number of operators, or the sequence of operations, that can be described in a single expression or formula, or in a single file for the CAG program instruction, may be limited to some prescribed limit.

It should be noted that the order of the items 202, 204, 206 in method 200 may be different from the example discussed. For example, in other embodiments, item 204 may be performed before item 202, or simultaneously with item 202.

Also, it should be noted that the operators that may be used in the program CAG instruction are not limited to the examples described, and that there may be other operators in the CAG program instruction. FIG. 7 illustrates a list 700 of examples of operators in the CAG language that may be used in/to create the CAG program instruction. There may be other examples, and therefore the list 700 should not be treated as an exhaustive list. In some embodiments, a CAG program instruction may include one or a combination of the operators listed in the list 700. As shown in the figure, examples of the operators that may be used in the CAG program instruction include a margin operator 702, an union operator 704, a hull operator 706, a smooth operator 708, a margin anisotropic operator 710, a subtract operator 712, an intersect operator 714, a shift operator 716, a rotate operator 718, a scale operator 720, a block operator 722, a sphere operator 724, and a cylinder operator 726.

The margin operator 702 is configured to return a new object by adding a margin around a given object that is spaced away from the given object a certain prescribed distance.

The union operator 704 is configured to return a new object that is a union of a given list of objects.

The hull operator 706 is configured to return a new object by generating a hull with a curvature having a prescribed maximum allowable radius.

The smooth operator 708 is configured to return a new object by smoothing a surface of a given object based on a certain "radius" input.

The margin anisotropic operator 710 is configured to return a new object by adding a margin at a certain prescribed distance away from a given object only in a given direction with respect to the given object.

The subtract operator 712 is configured to return a new object that includes all voxels of one object (object 1) that are not in another object (object2).

The intersect operator 714 is configured to return a new object that is the intersection of all objects in a given list.

The shift operator 716 is configured to return a new object that corresponds to a given object shifted by a given vector (including a direction and an amount of shift).

The rotate operator 718 is configured to return a new object that corresponds to a given object rotated by alpha, phi, and theta, which are the prescribed rotation about three different respective axes that are perpendicular to each other.

The scale operator 720 is configured to return a new object by scaling a given object for a certain prescribed factor.

The block operator 722 is configured to return a new object that has a shape of a block of a given size at a given position.

The sphere operator 724 is configured to return a new object that has a shape of a sphere of a given radius.

The cylinder operator 726 is configured to return a new object that has the shape of a cylinder defined by an axis starting point, an axis ending point, and a radius. The created cylinder will have a longitudinal axis extending from the axis starting point to the axis ending point, and the prescribed radius.

In some embodiments, one or more of the above operators may be used in a formula that defines the CAG program instruction for operating on the medical image. In other embodiments, one or more of the above operators may be used in a script that defines the CAG program instruction for operating on the medical image. In further embodiments, one or more of the above operators may be used in a graphical representation that defines the CAG program instruction for operating on the medical image.

Figure 8:
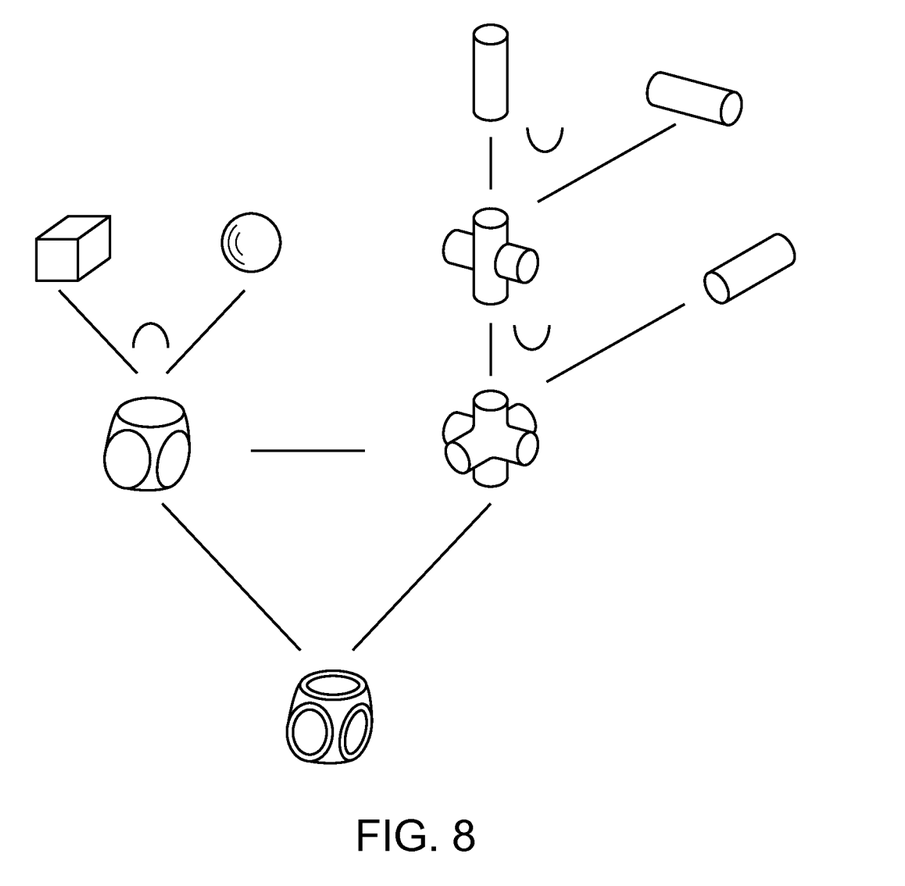
FIG. 8 illustrates an example of a constructive geometry tree.

In some embodiments, the CAG language for supporting (e.g., creating) the CAG program instruction for operating on the medical image may use the concept of constructive solid geometry. Constructive solid geometry may be used to define and/or manipulate solid objects that are composed of multiple simple objects. Constructive solid geometry uses composition operations (such as union, intersection, and subtraction) and operations on single objects (such as translation, rotation, and scaling). An example of an object described using a constructive solid geometry tree is illustrated in FIG. 8.

Also, in some embodiments, the CAG program instruction may include one or more mathematical operators (e.g., $+$, $-$, $*$, $/$, sin, cos, tan, $\sin^{-1}$, $\cos^{-1}$, $\tan^{-1}$, integral, derivative, etc.). In other embodiments, the CAG program instruction may include one or more logical operators. Thus, the CAG program instruction may include one or more operators for processing one or more geometric objects, one or more mathematical operators, and/or one or more logical operators in different embodiments. Also, in some embodiments, the different operators that may be used in the CAG program instruction may work with numbers, variables (e.g., logical and/or string variables), vectors, geometric objects, and/or combination thereof.

Also, in one or more embodiments described herein, the CAG program instruction may include an instruction for one or more loops. For example, the CAG program instruction for operating on the medical image may include FOR instruction, STEP instruction, WHILE instruction and/or END WHILE instruction.

In addition, in one or more embodiments described herein, the CAG program instruction for operating on the medical image may include a conditional instruction. For example, the CAG program instruction may include IF-THEN instruction, ELSE instruction, and/or END IF instruction.

In some embodiments, the concept of the CAG program instruction is very easy to learn, because it has a very small set of data types and operations. For example, in some embodiments, the CAG language supporting the CAG program instruction may be simpler (e.g., less extensive and versatile) than C++ language. Because the CAG program instruction is easy to use and understand, professionals of medical imaging or anatomical fields may immediately understand and use the CAG language of the CAG program instruction (especially in its graphical form), without any need for extensive training or computing knowledge.

In the above embodiments, one or more of the operators in the CAG program instruction, when executed by the processing unit 12, return a new geometric object. Thus, in some embodiments, it may be beneficial to have a memory management mechanism, such as a garbage collector, to dispose objects that are no longer used. For example, in the above example of FIG. 3, after the new object 460 is created, the previous intermediate objects 450, 452, 454 may be disposed in the garbage collector process.

Also, in some embodiments, the above method 200 may be performed during a treatment planning session (e.g., during simulation, optimization, etc.). For example, in some embodiments, an image may be analyzed to identify target volume and organs at risk. Such may be accomplished by a technician reviewing the image and/or by a processing unit that performs automatic segmentation. Alternatively, interested structure may be obtained using atlas-based segmentation. For example, an initial shape of a mamma target volume of an actual patient may be obtained by deforming a previously determined target volume of another patient (the atlas patient). After structures of interest in the image are determined, a cleanup procedure may be performed that involves the method 200 of FIG. 2. For example, in some embodiments, the CAG program instruction obtained in item 204 for operating on the medical image may prescribe a sequence of operations, such as removal of small, isolated parts, smoothing of surfaces, application of margins, and removal of undesired overlap with other structures in the image. Also, in other embodiments, the CAG program instruction obtained in item 204 for operating on the medical image may prescribe two or more target volumes be combined, wherein the target volumes may be identified by a radiotherapist and/or identified automatically by a processing unit (e.g., the processing unit 12). In further embodiments, the method 200 of FIG. 2 may be performed automatically during an automatic segmentation.

After a treatment plan is determined using the output of the executed CAG program instruction (e.g., obtained from item 206 of FIG. 2), the treatment plan may then be executed using a radiation system to deliver radiation to a patient.

Radiation System

Figure 9:
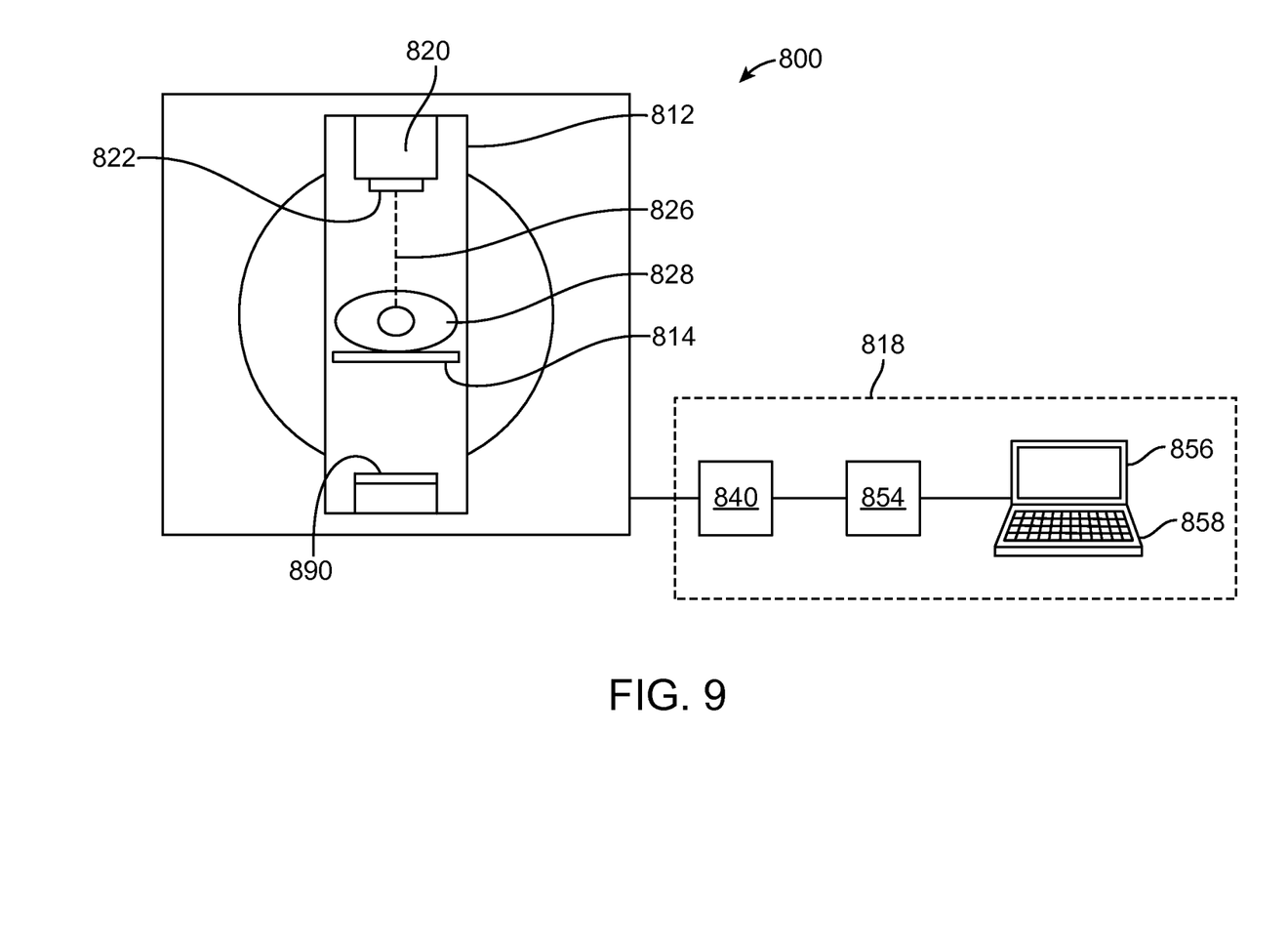
FIG. 9 illustrates an example of a radiation system.

FIG. 9 illustrates a radiation system 800 in accordance with some embodiments. The system 800 includes a gantry 812 in a form of a rotating arm, a patient support 814 for supporting a patient 828, and a control system 818 for controlling an operation of the gantry 812. In the illustrated embodiments, the gantry 812 has a C-arm configuration. In other embodiments, the gantry 812 may have a slip-ring configuration (donut shape with a bore). The system 800 also includes a radiation source (e.g., x-ray source) 820 that projects a beam 826 of radiation towards the patient 828, and a collimator 822 for changing a shape of the beam. The system 800 also includes a detector 890 on an opposite side of the gantry 812, which in some cases, may be used to receive radiation exiting from the patient 828, and generate image(s) using the received radiation. The detector 890 has a plurality of sensor elements configured for sensing a x-ray that passes through the patient 828. Each sensor element generates an electrical signal representative of an intensity of the x-ray beam as it passes through the patient 828. In other embodiments, the system 800 does not include the detector 890.

In the illustrated embodiments, the radiation source 820 is a treatment radiation source for providing treatment energy. In other embodiments, the radiation source 820 may be a diagnostic radiation source for providing diagnostic energy (e.g., energy that is suitable for generating an image). In further embodiments, the radiation source 820 can be configured to selectively provide treatment energy and diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 820 is able to generate X-ray radiation at a plurality of photon energy levels within a range anywhere between approximately 10 keV and approximately 20 MeV.

The control system 818 includes a processor 854, such as a computer processor, coupled to a source rotation control 840. The control system 818 may also include a monitor 856 for displaying data and an input device 858, such as a keyboard or a mouse, for inputting data. During a scan to acquire x-ray projection data (e.g., cone beam CT image data), the source 820 rotates about the patient 828. The rotation of the source 820 and the operation of the radiation source 820 are controlled by the source rotation control 840, which provides power and timing signals to the radiation source 820 and controls a rotational speed and position of the source 820 based on signals received from the processor 854. Although the control 840 is shown as a separate component from the gantry 812 and the processor 854, in alternative embodiments, the control 840 can be a part of the gantry 812 or the processor 854.

During a radiation procedure, the radiation source 820 generates and directs an x-ray beam 826 towards the patient 828, while the detector 890 measures the x-ray absorption at a plurality of transmission paths defined by the x-ray beam during the process. The detector 890 produces a voltage proportional to the intensity of incident x-rays, and the voltage is read and digitized for subsequent processing in a computer. In some embodiments, the image from the detector 890 may be used to confirm a radiation delivery after or during a session. In other embodiments, the image from the detector 890 may be analyzed to determine an effect of a radiation delivery, and future treatment plan may be modified based on a result of the analysis.

In the above embodiments, the executed CAG program instruction to operate on a medical image has been described as being for radiation treatment planning. In other embodiments, the executed CAG program instruction may be for other types of treatment planning that does not involve radiation. For example, in other embodiments, the CAG program instruction may be for operating on a medical image for proton treatment planning. In further embodiments, instead of using the output of the executed CAG program instruction for treatment planning, the output of the executed CAG program instruction may be for analyzing anatomical structures. For example, in some embodiments, the CAG program instruction may be entered and/or executed at a workstation where a person needs to calculate properties of some delineated structures of interest in the medical image.

In some of the embodiments described herein, the CAG program instruction for operating on the medical image has been described as being for creating an object in the image. In some embodiments, the creating of the object may be accomplished by adding a new object to the image. In other embodiments, the creating of the object may a part of a process to manipulate an object (e.g., moving or rotating an object), which may be accomplished by creating an object with a desired position and/or orientation, and deleting the previous object. In further embodiments, the creating of the object may be a part of a process to modify an object (e.g., scaling an object, shaping an object, smoothing an object, etc.), which may be accomplished by creating an object with the desired attributes, and deleting the previous object. Thus, the act of creating an object may be considered to be a sub-component of manipulating an object or modifying an object.

Computer System Architecture

Figure 10:
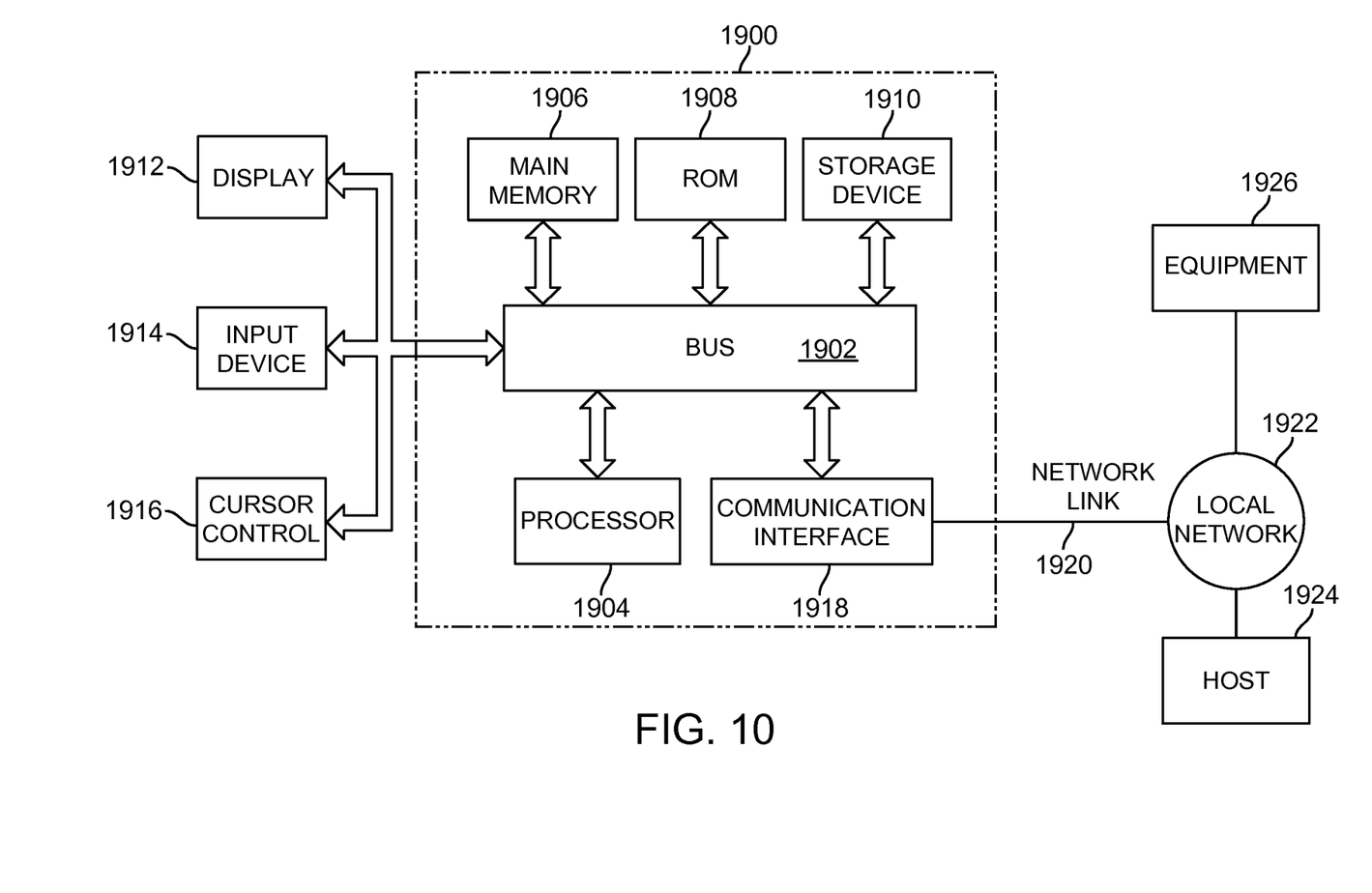
FIG. 10 illustrates a computer system.

FIG. 10 is a block diagram that illustrates an embodiment of a computer system 1900 upon which an embodiment of the invention may be implemented. Computer system 1900 includes a bus 1902 or other communication mechanism for communicating information, and a processor 1904 coupled with the bus 1902 for processing information. The processor 1904 may be an example of the processing unit 12 of FIG. 1, or another processor that is used to perform various functions described herein. For example, in some embodiments, the processor 1904 may be configured to perform one or more items described with reference to the method 200 of FIG. 2.

Returning to FIG. 10, the computer system 1900 also includes a main memory 1906, such as a random access memory (RAM) or other dynamic storage device, coupled to the bus 1902 for storing information and instructions to be executed by the processor 1904. The main memory 1906 also may be used for storing temporary variables or other intermediate information during execution of instructions to be executed by the processor 1904. The computer system 1900 further includes a read only memory (ROM) 1908 or other static storage device coupled to the bus 1902 for storing static information and instructions for the processor 1904. A data storage device 1910, such as a magnetic disk or optical disk, is provided and coupled to the bus 1902 for storing information and instructions.

The computer system 1900 may be coupled via the bus 1902 to a display 1912, such as a cathode ray tube (CRT) or a flat panel, for displaying information to a user. An input device 1914, including alphanumeric and other keys, is coupled to the bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The computer system 1900 may be used for performing various functions (e.g., calculation) in accordance with the embodiments described herein. According to one embodiment, such use is provided by computer system 1900 in response to processor 1904 executing one or more sequences of one or more instructions contained in the main memory 1906. Such instructions may be read into the main memory 1906 from another computer-readable medium, such as storage device 1910. Execution of the sequences of instructions contained in the main memory 1906 causes the processor 1904 to perform the process steps described herein. One or more processors in a multi-processing arrangement may also be employed to execute the sequences of instructions contained in the main memory 1906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1904 for execution. Such a medium may take many forms, including but not limited to, non-volatile media, volatile media, and transmission media. Non-volatile media includes, for example, optical or magnetic disks, such as the storage device 1910. A non-volatile medium may be considered as an example of a non-transitory medium. Volatile media includes dynamic memory, such as the main memory 1906. A volatile medium may be considered as another example of a non-transitory medium. Transmission media includes coaxial cables, copper wire and fiber optics, including the wires that comprise the bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1904 for execution. For example, the instructions may initially be carried on a magnetic disk of a remote computer. The remote computer can load the instructions into its dynamic memory and send the instructions over a telephone line using a modem. A modem local to the computer system 1900 can receive the data on the telephone line and use an infrared transmitter to convert the data to an infrared signal. An infrared detector coupled to the bus 1902 can receive the data carried in the infrared signal and place the data on the bus 1902. The bus 1902 carries the data to the main memory 1906, from which the processor 1904 retrieves and executes the instructions. The instructions received by the main memory 1906 may optionally be stored on the storage device 1910 either before or after execution by the processor 1904.

The computer system 1900 also includes a communication interface 1918 coupled to the bus 1902. The communication interface 1918 provides a two-way data communication coupling to a network link 1920 that is connected to a local network 1922. For example, the communication interface 1918 may be an integrated services digital network (ISDN) card or a modem to provide a data communication connection to a corresponding type of telephone line. As another example, the communication interface 1918 may be a local area network (LAN) card to provide a data communication connection to a compatible LAN. Wireless links may also be implemented. In any such implementation, the communication interface 1918 sends and receives electrical, electromagnetic or optical signals that carry data streams representing various types of information.

The network link 1920 typically provides data communication through one or more networks to other devices. For example, the network link 1920 may provide a connection through local network 1922 to a host computer 1924 or to equipment 1926 such as a radiation beam source or a switch operatively coupled to a radiation beam source. The data streams transported over the network link 1920 can comprise electrical, electromagnetic or optical signals. The signals through the various networks and the signals on the network link 1920 and through the communication interface 1918, which carry data to and from the computer system 1900, are exemplary forms of carrier waves transporting the information. The computer system 1900 can send messages and receive data, including program code, through the network(s), the network link 1920, and the communication interface 1918.

It should be noted that as used in this specification, the term "image", or a similar term, may refer to an image that is displayed in a screen, and/or to an image that is not displayed (such as image data that is stored in a medium). Similarly, the term "graphic", or a similar term, may refer to a graphic that is displayed in a screen, and/or to a graphic that is not displayed (such as graphical data that is stored in a medium). Also, an image may be considered to be a graphic, or vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. A method involving a medical image, comprising:
   obtaining a medical image;
   obtaining a program instruction from a user for creating an object, wherein the program instruction is based on a constructive-anatomic-geometry (CAG) language;
   executing the program instruction to create the object, wherein the act of executing the program instruction is performed using a processor that is configured to process the CAG language;
   outputting graphical data representing the object that is created based on the program instruction for display in the image; and
   storing information regarding the object in a non-transitory medium;
   wherein the CAG language is any language having a plurality of commands that can be selectively combined for allowing one or more object-creation actions to be defined.

2. The method of claim 1, wherein the program instruction is in a form of a script.

3. The method of claim 1, wherein the program instruction is in a form of a formula.

4. The method of claim 1, wherein the program instruction is in a form of graphics.

5. The method of claim 1, wherein the program instruction comprises one or more operators for processing one or more geometric objects.

6. The method of claim 1, wherein the program instruction comprises one or more mathematical operators.

7. The method of claim 1, wherein the program instruction comprises one or more logical operators.

8. The method of claim 1, wherein the program instruction comprises an instruction for one or more loops.

9. The method of claim 1, wherein the program instruction comprises a conditional instruction.

10. The method of claim 1, wherein the program instruction is compatible with different medical software from different manufacturers.

11. The method of claim 1, wherein the program instruction is created using a language that is less versatile than C++ language.

12. The method of claim 1, wherein the object comprises an anatomical object, and the program instruction comprises instruction for creating a margin around the anatomical object in the image.

13. The method of claim 1, wherein the program instruction comprises instruction for combining two objects into a single object in the image.

14. The method of claim 1, wherein the program instruction comprises instruction for a hull operation.

15. The method of claim 1, wherein the program instruction comprises one or more of a margin operator, an union operator, a hull operator, a smooth operator, a margin anisotropic operator, a subtract operator, an intersect operator, a shift operator, a rotate operator, a scale operator, a block operator, a sphere operator, and a cylinder operator.

16. The method of claim 1, wherein the act of executing the program instruction is performed during a cleanup procedure in a treatment planning process.

17. The method of claim 1, wherein the act of executing the program instruction is performed automatically during an automatic segmentation.

18. The method of claim 1, wherein the object comprises an outline for one or more tissue structures.

19. The method of claim 1, wherein the obtained image comprises the object, the object being artificially created.

20. The method of claim 1, wherein the program instruction is stored as a sequence of characters in a first environment, and the method further comprises loading the program instruction in a second environment for execution.

21. The method of claim 1, wherein the program instruction contains a set of one or more object creation instructions created by the user.

22. The method of claim 1, wherein the program instruction is based on a specialized language designed for creating and manipulating graphical objects.

23. The method of claim 1, wherein the one or more object-creation actions comprise an action to add an object portion to an object, an action to delete the object portion from the object, or an action to change a shape of the object.

24. A computer product having a non-transitory medium storing a set of instructions, an execution of which causes a method to be performed, the method comprising:
   obtaining a medical image;
   obtaining a program instruction from a user for creating an object, wherein the program instruction is based on a constructive-anatomic-geometry (CAG) language;
   executing the program instruction to create the object; and
   outputting graphical data representing the object that is created based on the program instruction for display in the image;
   wherein the CAG language is any language having a plurality of commands that can be selectively combined for allowing one or more object-creation actions to be defined.

25. The computer product of claim 24, wherein the program instruction is in a form of a script, a formula, or graphics.

26. The computer product of claim 24, wherein the program instruction comprises one or more operators for processing one or more geometric objects.

27. The computer product of claim 24, wherein the program instruction comprises one or more mathematical operators.

28. The computer product of claim 24, wherein the program instruction comprises one or more logical operators.

29. The computer product of claim 24, wherein the program instruction comprises an instruction for one or more loops.

30. The computer product of claim 24, wherein the program instruction comprises a conditional instruction.

31. The computer product of claim 24, wherein the program instruction is compatible with different medical software from different manufacturers.

32. The computer product of claim 24, wherein the program instruction is created using a language that is less versatile than C++ language.

33. The computer product of claim 24, wherein the object comprises an anatomical object, and the program instruction comprises instruction for creating a margin around the anatomical object in the image.

34. The computer product of claim 24, wherein the program instruction comprises instruction for combining two objects into a single object in the image.

35. The computer product of claim 24, wherein the program instruction comprises instruction for a hull operation.

36. The computer product of claim 24, wherein the program instruction comprises one or more of a margin operator, an union operator, a hull operator, a smooth operator, a margin anisotropic operator, a subtract operator, an intersect operator, a shift operator, a rotate operator, a scale operator, a block operator, a sphere operator, and a cylinder operator.

37. The computer product of claim 24, wherein the act of executing the program instruction is performed during a cleanup procedure in a treatment planning process.

38. The computer product of claim 24, wherein the act of executing the program instruction is performed automatically during an automatic segmentation.

39. The computer product of claim 24, wherein the object comprises an outline for one or more tissue structures.

40. The computer product of claim 24, wherein the program instruction is stored as a sequence of characters in a first environment, and the method further comprises loading the program instruction into a second environment for execution.

41. The computer product of claim 24, wherein the program instruction contains a set of one or more object creation instructions created by the user.

42. The computer product of claim 24, wherein the program instruction is based on a specialized language designed for creating and manipulating graphical objects.

43. An apparatus, comprising:
a processor configured for
obtaining a medical image,
obtaining a program instruction from a user for creating an object, wherein the program instruction is based on a constructive-anatomic-geometry (CAG) language, wherein the CAG language is any language having a plurality of commands that can be selectively combined for allowing one or more object-creation actions to be defined;
executing the program instruction to create the object; and
outputting graphical data representing the object that is created based on the program instruction for display in the image; and
a non-transitory medium for storing information regarding the object.

44. The apparatus of claim 43, wherein the program instruction contains a set of one or more object creation instructions created by the user.

45. The apparatus of claim 43, wherein the program instruction is based on a specialized language designed for creating and manipulating graphical objects.

\* \* \* \* \*